(12) United States Patent
Hageman (10) Patent No.: US 11,707,478 B2
(45) Date of Patent: Jul. 25, 2023

(54) METHOD FOR INCREASING URIDINE CONCENTRATION IN BLOOD PLASMA

(71) Applicant: N.V. Nutricia, Zoetermeer (NL)

(72) Inventor: Robert Johan Joseph Hageman, Utrecht (NL)

(73) Assignee: N.V. Nutricia, Zoetermeer (NL)

( * ) Notice: Subject to any disclaimer, the term of this patent is extended or adjusted under 35 U.S.C. 154(b) by 55 days.

(21) Appl. No.: 16/327,741

(22) PCT Filed: Aug. 23, 2017

(86) PCT No.: PCT/NL2017/050553
§ 371 (c)(1),
(2) Date: Feb. 22, 2019

(87) PCT Pub. No.: WO2018/038609
PCT Pub. Date: Mar. 1, 2018

(65) Prior Publication Data
US 2019/0183916 A1    Jun. 20, 2019

(30) Foreign Application Priority Data
Aug. 23, 2016  (WO) ................ PCT/NL2016/050587

(51) Int. Cl.
*A61K 31/7072* (2006.01)
*A61K 9/08* (2006.01)
(Continued)

(52) U.S. Cl.
CPC ........ *A61K 31/7072* (2013.01); *A61K 9/0053* (2013.01); *A61K 9/0095* (2013.01);
(Continued)

(58) Field of Classification Search
None
See application file for complete search history.

(56) References Cited

U.S. PATENT DOCUMENTS

| 5,723,449 A | 3/1998 | Sommadossi et al. |
| 2005/0203053 A1* | 9/2005 | Wurtman ........... A61K 31/7072 514/51 |
| 2013/0295146 A1* | 11/2013 | Hageman ................ A23L 33/15 424/400 |

FOREIGN PATENT DOCUMENTS

| EP | 1800675 A1 | 6/2007 |
| WO | WO 2014/027882 A1 | 2/2014 |

OTHER PUBLICATIONS

Van Groeningen, C. J., et al. J. Nat. Cancer Inst. (1991), 83(6); 437-441.*

(Continued)

*Primary Examiner* — Kevin S Orwig
(74) *Attorney, Agent, or Firm* — N.V. Nederlandsch Octrooibureau; Catherine A. Shultz (57) ABSTRACT

The invention pertains to the use of soluble sodium in the manufacture of a composition or kit of parts for (therapeutically) improving and prolonging blood plasma uridine levels and tissue availability of uridine, and/or for treating or preventing impaired blood plasma uridine levels and tissue availability of uridine, and/or for preventing/treating disorders associated with impaired blood plasma and tissue availability of uridine, in a mammal, preferably a human being, by orally co-administering soluble sodium and uridine in a molar ratio of soluble sodium to uridine of more than 1:1, preferably more than 1.5:1, more preferably more than 2:1, even more preferably at least 2.5:1, even more preferably at least 2.8:1, more preferably 3:1-15:1, most preferably 3:1-10:1, particularly 3:1-5:1.

12 Claims, 3 Drawing Sheets

(51) Int. Cl.
   *A61K 47/12* (2006.01)
   *A61K 9/00* (2006.01)
   *A61K 33/14* (2006.01)
   *A61K 45/06* (2006.01)
   *A61P 7/00* (2006.01)
   *A61K 31/14* (2006.01)
   *A61K 31/202* (2006.01)
   *A61K 31/519* (2006.01)
   *A61K 31/675* (2006.01)
   *A61K 31/7105* (2006.01)
   *A61K 33/00* (2006.01)

(52) U.S. Cl.
   CPC ............ *A61K 9/08* (2013.01); *A61K 31/14* (2013.01); *A61K 31/202* (2013.01); *A61K 31/519* (2013.01); *A61K 31/675* (2013.01); *A61K 31/7105* (2013.01); *A61K 33/00* (2013.01); *A61K 33/14* (2013.01); *A61K 45/06* (2013.01); *A61K 47/12* (2013.01); *A61P 7/00* (2018.01)

(56) References Cited

OTHER PUBLICATIONS

Venhoff, N, et al. AIDS (2005), 19; 739-745.*
Slugoski, M. D., et al. J. Biol. Chem. (2009), 284(25), 17266-17280.*
Klubes et al., "Comparison of the bioavailability of uridine in mice after either oral or parenteral administration", Cancer Chemotherapy Pharmacology, vol. 17, No. 3, Jul. 1, 1986, pp. 236-240.
Hasnain et al., "Metabolic studies of uridine in rats with doca-salt hypertension and on high sodium diet", Clinical and Experimental Pharmacology and Physiology, vol. 20, No. 5, a May 1993, pp. 384-387.
International Search Report issued in PCT/NL2017/050553, dated Nov. 10, 2017.
Written Opinion of the International Searching Authority issued in PCT/NL2017/050553, dated Nov. 10, 2017.

* cited by examiner

METHOD FOR INCREASING URIDINE CONCENTRATION IN BLOOD PLASMA

CROSS-REFERENCE TO RELATED APPLICATIONS

This application is the National Phase of International Patent Application No. PCT/NL2017/050553, filed Aug. 23, 2017, published on Mar. 1, 2018 as WO/2018/038609 A1, which claims priority to International Patent Application No. PCT/NL2016/050587, filed Aug. 23, 2016. The contents of these applications are herein incorporated by reference in their entirety.

FIELD OF THE INVENTION

The invention is in the field of medical nutrition, with the object of finding ways to improve uridine bioavailability in blood plasma and tissue, particularly in blood plasma and tissue, particularly plasma and brain tissue, of a mammal, preferably a human being.

BACKGROUND OF THE INVENTION

Uridine and its metabolites play a crucial role in a number of important metabolic pathways such as the endogenous synthesis of glycosylated compounds, carbohydrate homeostasis and membrane phospholipids (PLs). Its functions in the treatment of brain health problems have been reviewed in the art. PLs comprise phosphatidylcholines, phosphatidylethanolamines, phosphatidylinositols and phosphatoidylserines and can be synthesized by de novo synthesis of phosphatidylcholines and interconversions. Uridine, docosahexaenoic acid (DHA) and choline are involved to form the DHA-containing phosphatidylcholines. The enzymes catalyzing the formation of PC are not saturated at physiological conditions in humans and therefore increased blood levels of substrate components like uridine will increase the overall rate of PC biosynthesis.

It is generally known that uridine is strongly metabolized in the human body, directly or indirectly, e.g. by phosphorylation, conversion into cytidine or catabolism to uracil. Though it is metabolized in most cells, the liver appears to determine the uridine plasma concentrations to a great extent. Uridine is the main metabolite for inter-organ transport of uridine moieties and a constant high plasma concentration ensures ample supply of uridine for peripheral uridine use and metabolism. Therefore under normal physiological conditions uridine is found present in blood of different species. For example, the concentration in healthy individuals in blood after fasting is between about 4 and 8 µM but can be lower in malnourished, diseased or very old individuals. The concentration must be sufficiently high to be able to pass the membranes of mammalian cells and preferably be close to or even above the apparent Km value of its main transporter, which is CNT 1 in the gut and in many other cells, i.e. in the range of 6-16 µM, and for prolonged periods of time.

It is thus an object to provide a way to increase and maintain the concentration of uridine in blood to values of 6-16 µM, in order to have a high rate of influx of uridine into cells and a beneficial effect of uridine. Of note, oral administration of uridine has been reportedly attempted before, but with limited success. Klubes (Cancer Chemother Pharmacol. 1986 July; 17(3): 236-240) found low bioavailability (about 7%), and a highly variable response between individuals. As the clearance rate from blood is high (half-time is 3 to 4 hours), it requires administration of two or more doses per day in order to maintain uridine concentrations in blood plasma in the range of 6-16 µM.

Alternatively, based on the knowledge provided by Klubes (Cancer Chemother Pharmacol. 1986 July; 17(3): 236-240) large doses of uridine need be administered. There is however a limit to increasing the doses of uridine. At high concentrations, the benefits of uridine are hampered by toxic side effects including phlebitis, pyrogenic reactions and diarrhea. Attempting to increase uridine bioavailability, U.S. Pat. No. 5,567,689 and Safarjalani (Cancer Chemother Pharmacol. 2001 November; 48(5):389-97) seek solution in co-administering compounds that inhibit renal clearance of uridine or inhibit uridine phosphorylase to catabolize uridine to uracil, respectively. However, these inhibitors complicate administration protocols, but also demand a careful design per patient in order to induce plasma values above 4 µM, preferably between 6 and 16 µM. Some authors take yet a different path for increasing half-life by derivatization of the uridine source. Still it requires increased dosages and also repeated daily dosages.

WO 2014/027885 teaches that administration of UMP increases, controls and/or maintains fasting plasma uridine concentrations. Example 2 describes a composition with i.a. 625 mg UMP and 125 mg sodium content. In the field of treating neurodegenerative diseases, WO 2009/002164 describes the use of uridine or equivalent thereof for the prevention or delay of the onset of dementia in a prodromal dementia patient. The preferred uridine source is UMP. Example 3 describes a similar composition with i.a. 625 mg UMP and 125 mg sodium content. These numbers amount to a molar ratio of sodium:uridine of about 2.1, and about 95% of the sodium is provided as Na2UMP.

In the art there is a continuous need to improve uridine bioavailability in plasma and peripheral tissues such as brain tissue.

SUMMARY OF THE INVENTION

Figure 1:
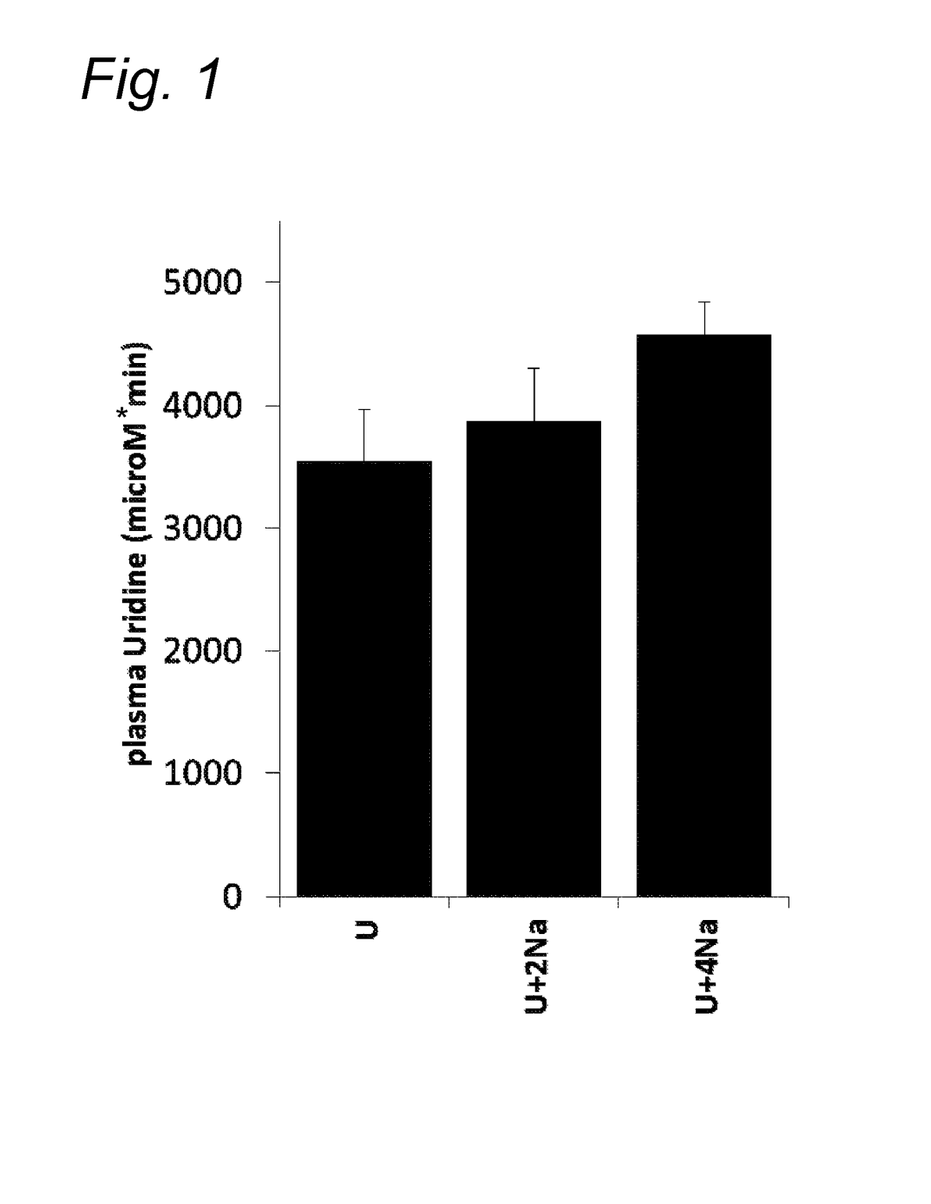
FIG. 1 is a histogram depicting the incremental area under the curve (iAUC) of blood plasma uridine concentration after oral administration of either uridine (U), uridine with two sodium ions per molecule uridine (U+2Na), or uridine with four sodium ions per molecule uridine, (U+4Na) depicted in micromolar*min. iAUC is the area under the blood plasma uridine concentration curve without the area beneath the baseline blood plasma uridine concentration. Error bars indicate s.e.m.
Figure 2:
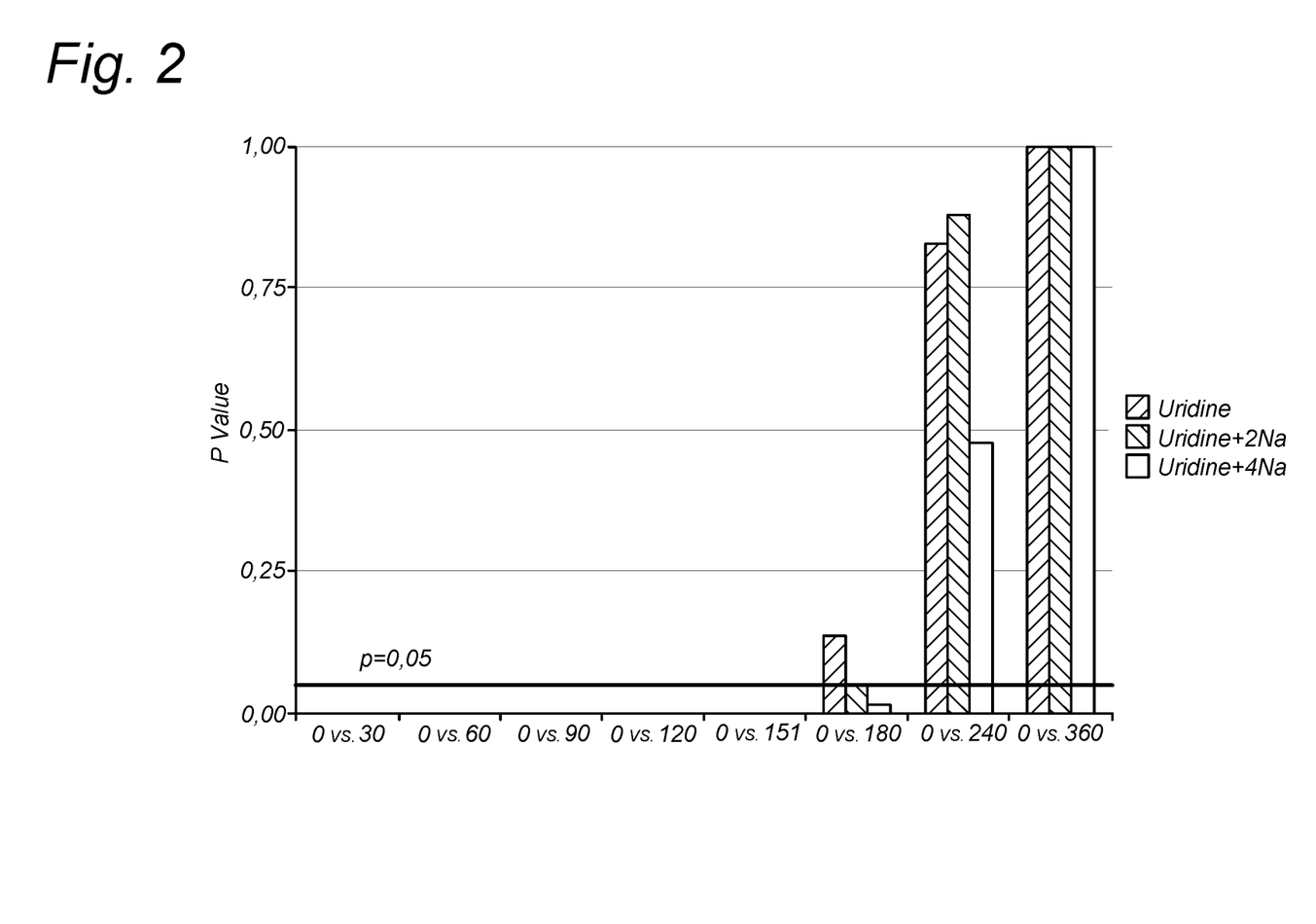
FIG. 2 is a histogram depicting p value calculated with posthoc Dunnett's multiple comparisons test when comparing baseline blood plasma uridine concentrations with indicated time points after oral administration of either uridine (Uridine), uridine with two sodium ions per molecule uridine (Uridine+2Na), or uridine with four sodium ions per molecule uridine, (Uridine+4Na). While oral administration of uridine is no longer statistically significantly above baseline levels after 151 minutes start of dosing uridine, at time 180 min Uridine+2Na has p=0.05 and Uridine+4Na is p<0.05 and are hence both statistically significantly above baseline levels. It provides indication that the addition of sodium ion prolongs the duration during which blood plasma uridine remains statistically significantly higher than the baseline than without the addition of sodium ions.

The inventors found that co-administering soluble sodium and uridine orally helps improving and prolonging blood plasma availability of the uridine in a mammal, preferably a human being, and it was found that uridine bioavailability was greatly improved and increased blood plasma levels of uridine extended over longer time spans when said uridine was co-administered with soluble sodium in a molar ratio of soluble sodium to uridine favouring the soluble sodium. Upon adding sodium both the amount of uridine made available to the blood was improved (FIG. 1) and the time for uridine blood plasma levels to return to base levels was extended (FIG. 2). The increased plasma bioavailability both in terms concentrations and over extended periods of time will make the uridine more accessible to tissue such as brain tissue. Reference is made to Cansev et al. "Oral uridine-5'-monophosphate (UMP) increases brain CDP-choline levels in gerbils" Brain Research (2005) 1058, pages 101-108. This is a surprising effect, considering that there has been little attention given to the sodium accompanying the preferred disodium uridine monophosphate in the art. When the skilled person would consider replace Na2UMP by uridine in the art, sodium levels would implicitly be reduced to molar ratios of sodium to uridine of about 0.1 only.

The inventors believe that the findings as detailed in the experimental section could be linked to the sodium-mediated nucleoside CNT transporters which are responsible for transporting nucleosides across the plasma membrane. The concentrative nucleoside transporters CNT1, CNT2 and CNT3 transport uridine and certain uridine analogues, but are otherwise in general selective for pyrimidine (CNT1) and purine (CNT2) nucleosides, with CNT3 being nonselective for purine and pyrimidine nucleosides. Both CNT1 and CNT2 display a 1:1 stoichiometry (nucleoside:sodium), while CNT3 on the other hand transports two sodium ions per nucleoside, and can also co-transport protons in a pH dependent manner in a 1:1 ratio. It is believed that it is the CNT1 and CNT2 transporters that are most involved in controlling uridine uptake from gut lumen into enterocytes and for many tissues from blood into peripheral tissues. In light thereof, the advantageous effects of sodium increasing blood plasma levels of uridine as observed by the present inventors going beyond the stoichiometric ratios of sodium to nucleoside as used with any of these transporters is all the more surprising. Also equilibrative transporters (ENT) are expressed on plasma membranes of many cell types, to transport uridine or other nucleosides. These transporters have no requirement for sodium. In fact, in the field of medical nutrition there is even further reluctance towards the use of much sodium: The inclusion of sodium in dietetic products is typically avoided in the art because it is believed to contribute to the potential risk to the development or maintenance of hypertension or may contribute to electrolyte disbalance e.g. in surgery patients or patients experiencing electrolyte infusions.

In one aspect, the invention thus pertains to the use of soluble sodium in the manufacture of a composition or kit of parts for (therapeutically) improving and prolonging blood plasma uridine levels and tissue availability of uridine in a mammal, preferably a human being in need thereof, and/or to treat or prevent impaired blood plasma and tissue availability of uridine in a mammal, preferably a human being, and disorders associated with impaired blood plasma and tissue availability of uridine in a mammal, preferably a human being, by orally co-administering soluble sodium and uridine in a molar ratio of soluble sodium to uridine of more than 1:1, preferably more than 1.5:1, more preferably more than 2:1, even more preferably at least 2.5:1, even more preferably at least 2.8:1, more preferably 3:1-15:1, most preferably 3:1-10:1, particularly 3:1-5:1. The advantages rest in (i) higher and earlier uridine peak levels, (ii) elevated plasma uridine levels over prolonged periods of time, and (iii) less variation in uridine absorption between individuals.

In the context of the invention, the term 'uridine' which refers to the compound that is administered (and measured in the blood) is understood to mean 1-beta-D-ribofuranosyl-uracil, i.e. 1-[(2R,3R,4S,5R)-3,4-dihydroxy-5-(hydroxymethyl)oxolan-2-yl]pyrimidine-2,4-dione. Where other forms or sources of uridine are intended, these are explicitly referred to as such (i.e. forms or sources of uridine), or referred to as uridine derivatives or uridine equivalents.

Within the context of the invention, the term 'sodium' is understood to mean all food-grade soluble sodium provided or present in the composition or product or kit, which soluble sodium is released freely in the gut, such as sodium salts (chloride, sulphate, phosphate, hydroxide etc.) and sodium caseinate. Soluble sodium comprises mineral and organic salts, and refers to 'sodium in a form soluble in water' (water-soluble sodium). In one embodiment, the soluble sodium is dissolved sodium, i.e. $Na^+$ dissolved in water.

In the field of neurodegenerative disorders, and in the field of nutritional management of patients suffering from diabetes, insulin resistance and stroke, the benefits of the uridine together with specific ratios of soluble sodium to uridine in improving and prolonging uridine bioavailability in blood plasma are left unattended in the art. In the aforementioned WO 2014/027885 and WO 2009/002164 the compositions comprise Na2UMP. It is thus an object of the invention thus to improve uridine tissue bioavailability and extend increased tissue levels of uridine, said tissue particularly being brain tissue.

It is particularly preferred to improve and extend blood plasma and tissue availability of uridine in mammal in need thereof, preferably a human being in need thereof, more preferably a human being at increased risk of or suffering from neurological disorders, preferably neurodegenerative disorders, preferably a brain disorder, like a dementia, brain ischemia or brain trauma, particularly a human being at risk of or suffering from impaired blood plasma and/or tissue availability of uridine. The tissue is preferably brain tissue.

In one embodiment, the co-administration of uridine and soluble sodium is directed to improving brain bioavailability of uridine.

LIST OF FIGURES

FIG. 1 indicates that there is an increasing trend in the available uridine concentration in blood plasma as the amount of sodium ions per molecule of uridine increases. More plasma uridine was available when uridine was administered with 2 or 4 sodium ions per molecule than when uridine was administered alone. A further increase in plasma uridine concentration was observed when the amount of sodium ions per molecule uridine increased from 2 to 4.

FIG. 3 shows that after the oral administration of Uridine, the blood plasma uridine concentration returned more quickly to baseline levels (151 min), compared to 180 minutes for Uridine +2Na. While the blood plasma uridine concentrations for both Uridine+2Na and Uridine+4Na were statistically significant above baseline levels for 180 min after oral administration, at 180 min the Uridine+4Na was still more statistically significant above baseline ($p<0.05$) than the Uridine+2Na ($p=0.05$) (see FIG. 2). At the next measuring point of 240 min, both the Uridine+2Na and Uridine+4Na were no longer statistically significant above baseline levels ($p>0.05$), but still the Uridine+4Na sample had a better statistical significance ($p=0.48$ vs. $p=0.89$). It is therewith deducted that Uridine+4Na sample stayed longer statistically significant above baseline levels after the 180 min measuring point than the Uridine+2Na sample, thus further prolonging the blood plasma uridine concentration. The same trends as in FIGS. 1 and 2 were observed.

LIST OF EMBODIMENTS

1. Use of soluble sodium in the manufacture of a composition or kit of parts for (therapeutically) improving and prolonging blood plasma uridine levels and tissue availability of uridine, and/or for treating or preventing impaired blood plasma uridine levels and tissue availability of uridine, and/or for preventing/treating disorders associated with impaired blood plasma and tissue availability of uridine, in a mammal, preferably a human being, by orally co-administering soluble sodium and uridine in a molar ratio of soluble sodium to uridine of more than 1:1, preferably more than 1.5:1, more preferably more than 2:1, even more preferably at least 2.5:1, even more preferably at least 2.8:1, more preferably 3:1-15:1, most preferably 3:1-10:1, particularly 3:1-5:1.
2. Use according to embodiment 1, wherein said human being is at increased risk of or suffering from neurological disorders including neurodegenerative disorders or brain trauma; diabetes; insulin resistance; stroke; endothelial damage; or fatty liver.
3. Use according to any one of the preceding embodiments, wherein said uridine is provided in therapeutic amounts, preferably in an amount of about 30-1000 mg per day, preferably about 100-900 mg per day, preferably about 200-800 mg, more preferably about 300-700 mg per day.
4. Use according to any one of the preceding embodiments, further administering at least one of docosahexaenoic acid (22:6; DHA), eicosapentaenoic acid (20:5; EPA) and docosapentaenoic acid (22:5; DPA), or esters thereof.
5. Use according to embodiment 5, further administering at least DHA, preferably in therapeutic amounts, preferably in an amount of at least 50 mg per day, more preferably at least 100 mg per day, more preferably 500 to 5000 mg per day, more preferably 750 to 4000 mg per day, most preferably 1000 to 3000 mg per day.
6. Use according to any of the preceding embodiments, said tissue being brain tissue.
7. Use of soluble sodium in the manufacture of a composition or kit of parts for (therapeutically) improving brain availability of uridine by orally co-administering soluble sodium and uridine to a mammal, preferably a human being, by orally co-administering soluble sodium and uridine in a molar ratio of soluble sodium to uridine of more than 1:1, preferably more than 1.5:1, more preferably more than 2:1, even more preferably at least 2.5:1, even more preferably at least 2.8:1, more preferably 3:1-15:1, most preferably 3:1-10:1, particularly 3:1-5:1.
8. Use according to any of the preceding embodiments, wherein said mammal is a human being that suffers from or is at risk of a memory and/or cognitive disorder, memory decline and/or cognitive dysfunction, such as Age Associated Memory Impairment (AAMI); Alzheimer's Disease; Parkinson's disease; Pick's disease; and/or dementia, including vascular dementia, frontotemporal dementia, semantic dementia or dementia with Lewy bodies, and/or Mild Cognitive Impairment (MCI), more preferably said mammal is a human being that suffers from or is at risk of Alzheimer's Disease or dementia.
9. Use according to any of the preceding embodiments, said composition or kit of parts further comprising at least one, or preferably both of:
   choline, or salts or esters thereof; and
   at least one vitamin B selected from the group of vitamin B6, vitamin B12 and vitamin B9, or equivalents thereof, preferably at least vitamins B6 and B9, most preferably vitamins B6, B9 and B12.
10. Use according to any of the preceding embodiments, said composition or kit of parts further comprising therapeutic amounts of choline, or a salt or ester thereof, preferably at least 50 mg choline per day.
11. Use of soluble sodium in the manufacture of a composition or kit of parts for (therapeutically) improving and prolonging blood plasma uridine levels and tissue availability of uridine, and/or for treating or preventing impaired blood plasma uridine levels and tissue availability of uridine, and/or for preventing/treating disorders associated with impaired blood plasma and tissue availability of uridine, in a mammal, preferably a human being, by orally co-administering soluble sodium and uridine and/or one or more sodium-free uridine derivatives selected from the group consisting of deoxyuridine, uridine nucleotide (preferably UMP), and RNA, in a molar ratio of soluble sodium to uridine of more than 1:1, preferably more than 1.5:1, more preferably more than 2:1, even more preferably at least 2.5:1, even more preferably at least 2.8:1, more preferably 3:1-15:1, most preferably 3:1-10:1, particularly 3:1-5:1.
12. Use of soluble sodium in the manufacture of a composition or kit of parts for (therapeutically) improving and prolonging blood plasma uridine levels and tissue availability of uridine, and/or for treating or preventing impaired blood plasma uridine levels and tissue availability of uridine, and/or for preventing/treating disorders associated with impaired blood plasma and tissue availability of uridine, in a mammal, preferably a human being, by co-administering disodium uridine monophosphate (Na2UMP) and/or sodium uridine diphosphate (NaUDP), preferably at least Na2UMP, optionally in combination with uridine and/or one or more sodium-free uridine derivatives, with soluble sodium:
   (i) in a molar ratio of added soluble sodium (i.e. other than soluble sodium provided in the form of Na2UMP and NaUDP) to uridine (as the sum of uridine (i.e. the ribosyl uracil) calculated from Na2UMP, NaUDP, and the optional uridine and sodium-free uridine derivatives) of more than 1:1, preferably more than 1.5:1, more preferably more than 2:1, more preferably at least 2.5:1, more preferably at least 2.8:1, more preferably 3:1-15:1, most preferably 3:1-10:1, particularly 3:1-5:1; and/or (ii) in a molar ratio of total soluble sodium (as the sum of sodium provided in the form of Na2UMP and NaUDP, and added soluble sodium) to uridine (as the sum of uridine (i.e. the ribosyl uracil) calculated from Na2UMP, NaUDP, and the optional uridine and sodium-free uridine derivatives) of at least 2.5:1, more preferably at least 2.8:1, more preferably 3:1-15:1, most preferably 3:1-10:1, particularly 3:1-5:1, particularly at least 4:1, and wherein the composition or kit preferably comprises a total amount of uridine of about 30-1000 mg uridine per ml, preferably about 100-900 mg uridine per 100 ml, preferably about 200-800 mg uridine per 100 ml, more preferably about 300-700 mg uridine per 100 ml.

13. A nutritional composition or nutritional product or kit of parts comprising uridine and soluble sodium in a molar ratio of soluble sodium to uridine of more than 1:1, preferably more than 1.5:1, more preferably more than 2:1, even more preferably 2.5:1-15:1, more preferably at least 2:8:1, more preferably 3:1-10:1, most preferably 3:1-5:1, wherein the composition, product or kit comprises a total amount of uridine of about 30-1000 mg uridine per ml, preferably about 100-900 mg uridine per 100 ml, preferably about 200-800 mg uridine per 100 ml, more preferably about 300-700 mg uridine per 100 ml, said composition or product or kit preferably further comprising:

at least one of docosahexaenoic acid (22:6; DHA), eicosapentaenoic acid (20:5; EPA) and docosapentaenoic acid (22:5; DPA), or esters thereof; and/or at least one, or preferably both of:
  choline, or salts or esters thereof; and
  at least one vitamin B selected from the group of vitamin B6, vitamin B12 and vitamin B9, or equivalents thereof, preferably at least vitamins B6 and B9, most preferably vitamins B6, B9 and B12.

14. The nutritional composition or nutritional product or kit of parts according to embodiment 13, comprising at least 50 mg, more preferably at least 100 mg, more preferably 500-5000 mg DHA, more preferably 750-4000 mg DHA, even more preferably 1000-3000 mg DHA per 100 ml.

15. The nutritional composition or nutritional product or kit of parts according to any one of embodiments 13-14, wherein sodium and uridine are present in a molar ratio of soluble sodium to uridine of at least 3:1, preferably at least 3.5:1, most preferably at least 4:1.

16. The nutritional composition or nutritional product or kit of parts according to any one of embodiments 13-15, comprising choline, or a salt or ester thereof, preferably 80 mg to 3000 mg choline per 100 ml of the composition or combination, preferably 100 mg to 2000 mg choline per 100 ml, preferably 200 to 1000 mg choline per 100 ml, most preferably 200 mg to 600 mg choline per 100 ml.

17. A combination of uridine and soluble sodium in a molar ratio of soluble sodium to uridine of more than 1:1, preferably more than 1.5:1, more preferably more than 2:1, even more preferably 2.5:1-15:1, more preferably at least 2:8:1, more preferably 3:1-10:1, most preferably 3:1-5:1.

18. A nutritional product comprising the combination of embodiment 17, said product having a molar ratio of soluble sodium to uridine of more than 1:1, preferably more than 1.5:1, more preferably more than 2:1, even more preferably 2.5:1-15:1, more preferably at least 2:8:1, more preferably 3:1-10:1, most preferably 3:1-5:1, wherein the product comprises a total amount of uridine of about 30-1000 mg uridine per ml, preferably about 100-900 mg uridine per 100 ml, preferably about 200-800 mg uridine per 100 ml, more preferably about 300-700 mg uridine per 100 ml.

19. A method for improving and prolonging blood plasma uridine levels and tissue availability of uridine, and/or for treating or preventing (including reducing the risk of) impaired blood plasma uridine levels and tissue availability of uridine, and/or for preventing (including reducing the risk of) or treating disorders associated with impaired blood plasma and tissue availability of uridine, in a mammal, preferably a human being, by orally co-administering soluble sodium and uridine in a molar ratio of soluble sodium to uridine of more than 1:1, preferably more than 1.5:1, more preferably more than 2:1, even more preferably at least 2.5:1, even more preferably at least 2.8:1, more preferably 3:1-15:1, most preferably 3:1-10:1, particularly 3:1-5:1.

20. A (nutritional) composition or kit of parts, preferably a composition, for use in (therapeutically) improving and prolonging blood plasma uridine levels and tissue availability of uridine, and/or in treating or preventing impaired blood plasma uridine levels and tissue availability of uridine, and/or in preventing/treating disorders associated with impaired blood plasma and tissue availability of uridine, in a mammal, preferably a human being, said kit of parts or composition comprising soluble sodium and uridine in a molar ratio of soluble sodium to uridine of more than 1:1, preferably more than 1.5:1, more preferably more than 2:1, even more preferably at least 2.5:1, more preferably at least 2.8:1, more preferably 3:1-15:1, most preferably 3:1-10:1, particularly 3:1-5:1.

21. A combination of uridine and soluble sodium for (therapeutic) use in improving and prolonging blood plasma uridine levels and tissue availability of uridine, and/or in treating or preventing impaired blood plasma uridine levels and tissue availability of uridine, and/or in preventing/treating disorders associated with impaired blood plasma and tissue availability of uridine, in a mammal, preferably a human being, wherein soluble sodium and uridine are co-administered in a molar ratio of soluble sodium to uridine of more than 1:1, preferably more than 1.5:1, more preferably more than 2:1, even more preferably at least 2.5:1, more preferably at least 2.8:1, more preferably 3:1-15:1, most preferably 3:1-10:1, particularly 3:1-5:1.

22. The (nutritional) composition or kit of parts according to embodiment 20, or the combination of uridine and soluble sodium according to embodiment 21, said tissue being brain tissue.

DETAILED DESCRIPTION OF THE INVENTION

In one aspect, the invention pertains to the use of soluble sodium in the manufacture of a composition or kit of parts for (therapeutically) improving and prolonging blood plasma and tissue availability of uridine in a mammal, preferably a human being in need thereof, and/or to treat or prevent impaired blood plasma and tissue availability of uridine in a mammal, preferably a human being in need thereof, by orally co-administering soluble sodium and uridine in a molar ratio of soluble sodium to uridine of more than 1:1, preferably more than 1.5:1, more preferably more than 2:1, more preferably at least 2.5:1, even more preferably at least 2.8:1, more preferably 3:1-15:1, most preferably 3:1-10:1, particularly 3:1-5:1. Uridine and soluble sodium may be co-administered in a composition or in a kit of parts, but co-administration together in a composition is preferred. In one embodiment, the kit comprises a first part (a) comprising uridine, and a second part (b) comprising soluble sodium. In a preferred embodiment, the tissue is brain tissue.

Worded differently, the invention pertains to a method for improving and prolonging blood plasma availability and availability to tissue of uridine in a mammal, and/or for treating or preventing (including reducing the risk of) impaired blood plasma and tissue availability of uridine in a mammal, preferably a human being, by orally co-administering soluble sodium and uridine in a molar ratio of soluble sodium to uridine of more than 1:1, preferably more than 1.5:1, more preferably more than 2:1, even more preferably at least 2.5:1, even more preferably at least 2.8:1, more preferably 3:1-15:1, most preferably 3:1-10:1, particularly 3:1-5:1. Also, the invention pertains to a (nutritional) composition or kit of parts, preferably a composition, for (therapeutic) use in improving and prolonging blood plasma and tissue availability of uridine in a mammal in need thereof, preferably a human being suffering from impaired blood plasma and tissue uridine levels, and/or for (therapeutic) use in treating or preventing impaired blood plasma and tissue availability of uridine in a mammal, preferably a human being, said kit of parts or composition comprising soluble sodium and uridine in a molar ratio of soluble sodium to uridine of more than 1:1, preferably more than 1.5:1, more preferably more than 2:1, even more preferably at least 2.5:1, more preferably at least 2.8:1, more preferably 3:1-15:1, most preferably 3:1-10:1, particularly 3:1-5:1. The invention also pertains to a combination of uridine and soluble sodium for (therapeutic) use in improving and prolonging blood plasma and tissue availability of uridine in a mammal in need thereof, preferably a human being suffering from impaired blood plasma and tissue uridine levels, and/or for (therapeutic) use in treating or preventing impaired blood plasma and tissue availability ofuridine in a mammal, preferably a human being, wherein soluble sodium and uridine are co-administered in a molar ratio of soluble sodium to uridine of more than 1:1, preferably more than 1.5:1, more preferably more than 2:1, even more preferably at least 2.5:1, more preferably at least 2.8:1, more preferably 3:1-15:1, most preferably 3:1-10:1, particularly 3:1-5:1. Evidence for improved and prolonged blood plasma availability of uridine is provided further below.

In the context of the invention, the tissue is preferably brain or other peripheral tissue expressing CNTs.

In one aspect, the invention pertains to the above use, method, combination or composition for use in (therapeutically) improving brain availability of uridine by orally co-administering soluble sodium and uridine to a mammal, preferably a human being, preferably a human being suffering from impaired blood plasma uridine levels, using the aforementioned molar ratios of sodium to uridine. In one aspect, the human being preferably suffers from or is at increased risk of impaired brain uridine levels. In one aspect, the invention pertains to the above method for improving brain availability of uridine by orally co-administering soluble sodium and uridine to a healthy mammal, preferably a healthy human being, preferably a human being in need of improving brain availability of uridine, preferably a healthy elderly person, preferably of at least 50 years of age, using the aforementioned molar ratios of sodium to uridine. The method may be a non-therapeutic method, improving physiological brain uridine levels, and co-administration of uridine and sodium may be in the form of a composition or a kit of parts, preferably a composition.

In view of the inventors' insights in the increased sodium to uridine molar ratios, the invention also pertains to a nutritional composition or nutritional product or kit of parts comprising uridine and soluble sodium in a molar ratio of soluble sodium to uridine of more than 1:1, preferably more than 1.5:1, more preferably more than 2:1, even more preferably 2.5:1-15:1, more preferably at least 2:8:1, more preferably 3:1-10:1, most preferably 3:1-5:1, said composition or product or kit further comprising:
at least one of docosahexaenoic acid (22:6; DHA), eicosapentaenoic acid (20:5; EPA) and docosapentaenoic acid (22:5; DPA), or esters thereof; and/or
at least one of, or preferably both of:
choline, or salts or esters thereof; and
at least one vitamin B selected from the group of vitamin B6, vitamin B12 and vitamin B9, or equivalents thereof, preferably vitamins B6 and B9, most preferably vitamins B6, B9 and B12.

The composition, product or kit preferably comprises about 30-1000 mg uridine per ml, preferably about 100-900 mg uridine per 100 ml, preferably about 200-800 mg uridine per 100 ml, more preferably about 300-750 mg uridine per 100 ml.

In a preferred aspect, the composition or product or kit is used in the methods or use of the invention as detailed herein.

Within the context of the invention, the term 'sodium' is understood to mean all food-grade soluble sodium provided or present in the composition or product or kit, which soluble sodium is released freely in the gut, such as sodium salts (chloride, sulphate, phosphate, hydroxide etc.) and sodium caseinate. Soluble sodium comprises mineral and organic salts, and refers to sodium in a form soluble in water. In one embodiment, the soluble sodium is dissolved sodium, i.e. $Na^+$ dissolved in water.

The role of soluble sodium in the context of uridine uptake particularly in the context of neurodegenerative disorders is unattended in the art, and the art promotes the use of UMP. Without any attention to the role of the soluble sodium in the art, there is little motivation for the skilled person for controlling the amount of sodium in the art in the event the skilled person would consider replacing the more favoured UMP for uridine. However, the inventors found that the blood plasma bioavailability of uridine is greatly improved if soluble sodium are co-administered with uridine, beyond the calculated molar sodium:uridine molar ratio of about 0.8 (1.6:1.9) in the art, preferably even above the theoretical molar amount of one molecule sodium per molecule of uridine that needs to pass the hCNT1 transporter.

The uridine is preferably provided in therapeutically effective amounts. The present use or method preferably involves the administration of about 30-1000 mg uridine per day, preferably about 300-900 mg uridine per day, preferably about 350-800 mg uridine per day, more preferably about 400-750 mg uridine per day. The present method or use preferably comprises the administration of a composition in liquid form, comprising about comprises about 30-1000 mg uridine per ml, preferably about 100-900 mg uridine per 100 ml, preferably about 200-800 mg uridine per 100 ml, more preferably about 300-700 mg uridine per 100 ml.

In terms of caloric content, the method, use and composition according to the invention preferably comprise about 30-1000 mg uridine, preferably about 100-900 mg uridine, more preferably about 200-800 mg uridine, even more preferably about 300-700 mg uridine per 100 kcal based on the total content of the composition administered.

Considering FSMP (Food for Special Medical Purposes) legislation it is preferred to maintain the molar ratio of total soluble sodium:uridine below 10:1, preferably below 9:1, more preferably below 8:1. This preferably applies to FSMP products, i.e. products which are deemed to comply with FSMP legislations.

Within the limits of the molar ratios of (added) soluble sodium to uridine according to the invention, it is preferred that soluble sodium levels in the use or method are preferably in the range of 20-500 mg, more preferably 50-250 mg per day or preferably in the range of 20-500 mg, more preferably 50-250 mg per 100 ml.

Uridine Derivatives

Sodium-Free Uridine Derivatives

In another aspect of the invention, a sodium-free uridine derivative is administered, preferably selected from the group consisting of deoxyuridine (deoxyribosyl uracil), uridine nucleotide (preferably UMP), and RNA (ribonucleic acid); more preferably selected from the group consisting of uridine nucleotide (preferably UMP), and RNA. A sodium-free uridine nucleotide is a uridine nucleoside with one or more phosphate groups provided without sodium counterions. For example, sodium-free UMP and UDP can be provided as K2UMP and KUDP, respectively.

In this embodiment, the invention pertains to the use of soluble sodium in the manufacture of a composition or kit of parts for (therapeutically) improving and prolonging blood plasma uridine levels and tissue availability of uridine, and/or for treating or preventing impaired blood plasma uridine levels and tissue availability of uridine, and/or for preventing/treating disorders associated with impaired blood plasma and tissue availability of uridine, in a mammal, preferably a human being, by orally co-administering soluble sodium and uridine and/or one or more sodium-free uridine derivatives selected from the group consisting of deoxyuridine, uridine nucleotide (preferably UMP), and RNA, in a molar ratio of soluble sodium to uridine of more than 1:1, preferably more than 1.5:1, more preferably more than 2:1, even more preferably at least 2.5:1, even more preferably at least 2.8:1, more preferably 3:1-15:1, most preferably 3:1-10:1, particularly 3:1-5:1.

Worded differently, in this embodiment, the invention pertains to a method for improving and prolonging blood plasma availability and availability to tissue of uridine in a mammal, and/or for treating or preventing (including reducing the risk of) impaired blood plasma and tissue availability of uridine in a mammal, preferably a human being, by orally co-administering soluble sodium and uridine and/or one or more sodium-free uridine derivatives selected from the group consisting of deoxyuridine, uridine nucleotide (preferably UMP), and RNA, with the above-mentioned molar ratio of soluble sodium to uridine. Also, the invention pertains to a (nutritional) composition or kit of parts, preferably a composition, for (therapeutic) use in improving and prolonging blood plasma and tissue availability of uridine in a mammal in need thereof, preferably a human being suffering from impaired blood plasma and tissue uridine levels, and/or for (therapeutic) use in treating or preventing impaired blood plasma and tissue availability of uridine in a mammal, preferably a human being, said kit of parts or composition comprising soluble sodium and uridine and/or one or more sodium-free uridine derivatives selected from the group consisting of deoxyuridine, uridine nucleotide (preferably UMP), and RNA, with the above-mentioned molar ratio of soluble sodium to uridine.

In these embodiments, the composition, kit, method or use according to the present invention preferably involves uridine selected from the group consisting of uridine and/or a sodium-free uridine derivative selected from the group consisting of deoxyuridine, uridine nucleotide (preferably UMP), and RNA. In these embodiments, the composition, kit, method or use according to the present invention does not include any Na2UMP and NaUDP. Preferably, the uridine provided in the composition, kit, method or use consists of uridine and/or one or more sodium-free uridine derivatives. In these embodiments, the uridine contributions to the molar ratio are understood to be defined in terms of uridine amounts (MW=244 g/mol), and the amount of uridine provided in the form of one or more of the above uridine derivatives can be recalculated.

The uridine is preferably provided in therapeutically effective amounts, and is calculated in terms of uridine. The present use or method preferably involves the administration of uridine and/or one or more sodium-free uridine derivatives including sodium-free uridine nucleotides, wherein the cumulative amount of uridine and sodium-free uridine derivatives is 30-1000 mg uridine per day, preferably about 300-900 mg uridine per day, preferably about 350-800 mg uridine per day, more preferably about 400-750 mg uridine per day. The present method or use preferably comprises the administration of a composition in liquid form, comprising uridine and/or uridine derivatives, wherein the cumulative amount of uridine and sodium-free uridine derivatives is about 30-1000 mg uridine per ml, preferably about 100-900 mg uridine per 100 ml, preferably about 200-800 mg uridine per 100 ml, more preferably about 300-700 mg uridine per 100 ml. In terms of caloric content, the present method, use and composition preferably comprises the administration of a composition in liquid form, comprising uridine and/or uridine derivatives, wherein the cumulative amount of uridine and sodium-free uridine derivatives is about 30-1000 mg uridine, preferably about 100-900 mg uridine, more preferably about 200-800 mg uridine, even more preferably about 300-700 mg uridine per 100 kcal based on the total content of the composition administered.

In view of the inventors' insights in the increased sodium to uridine molar ratios, the uridine derivatives can be used to provide a nutritional composition or nutritional product or kit of parts comprising uridine and/or one or more sodium-free uridine derivatives, and soluble sodium, in a molar ratio of soluble sodium to uridine as defined here above, said composition or product or kit further comprising:

at least one of docosahexaenoic acid (22:6; DHA), eicosapentaenoic acid (20:5; EPA) and docosapentaenoic acid (22:5; DPA), or esters thereof, and/or     at least one of, or preferably both of:

choline, or salts or esters thereof; and         at least one vitamin B selected from the group of vitamin B6, vitamin B12 and vitamin B9, or equivalents thereof, preferably vitamins B6 and B9, most preferably vitamins B6, B9 and B12.

The method or use according to these embodiments also pertains to improving uridine tissue bioavailability and extending increased tissue levels of uridine, said tissue particularly being brain tissue, using uridine and/or one or more uridine derivatives in molar ratios of soluble sodium to uridine as defined here above.

Sodium-Uridine Derivatives: NaUDP, Na2UMP

As a separate embodiment, the invention also pertains to a method or use of soluble sodium in the manufacture of a composition or kit of parts (said kit comprising (a) soluble sodium; and (b) disodium uridine monophosphate (Na2UMP) and/or sodium uridine diphosphate (NaUDP)), optionally in combination with uridine and/or one or more sodium-free uridine derivatives, for improving uridine blood plasma bioavailability and extending increased blood plasma levels of uridine by co-administering disodium uridine monophosphate (Na2UMP) and/or sodium uridine diphosphate (NaUDP), preferably at least Na2UMP, optionally in combination with uridine and/or one or more sodium-free uridine derivatives, with soluble sodium:

(i) in a molar ratio of added soluble sodium (i.e. other than soluble sodium provided in the form of Na2UMP and NaUDP) to uridine (as the sum of uridine (i.e. the ribosyl uracil) calculated from Na2UMP, NaUDP, and the optional uridine and sodium-free uridine derivatives) of more than 1:1, preferably more than 1.5:1, more preferably more than 2:1, more preferably at least 2.5:1, more preferably at least 2.8:1, more preferably 3:1-15:1, most preferably 3:1-10:1, particularly 3:1-5:1; and/or (ii) in a molar ratio of total soluble sodium (as the sum of sodium provided in the form of Na2UMP and NaUDP, and added soluble sodium) to uridine (as the sum of uridine (i.e. the ribosyl uracil) calculated from Na2UMP, NaUDP, and the optional uridine and sodium-free uridine derivatives) of at least 2.5:1, more preferably at least 2.8:1, more preferably 3:1-15:1, most preferably 3:1-10:1, particularly 3:1-5:1, particularly at least 4:1.

In this embodiment, the composition or kit preferably comprises about 30-1000 mg uridine per ml, preferably about 100-900 mg uridine per 100 ml, preferably about 200-800 mg uridine per 100 ml, more preferably about 300-700 mg uridine per 100 ml.

In the field of neurodegenerative disorders, and in the field of nutritional management of patients suffering from diabetes, insulin resistance and stroke, the benefits of sodium in improving and prolonging uridine bioavailability in blood plasma are left unattended in the art. In the aforementioned WO 2014/027885 and WO 2009/002164 the compositions comprise Na2UMP. While there are some soluble sodium present in the exemplified compositions, the amount of added sodium is about all traced back to the Na2UMP, and the molar ratio of total soluble sodium to uridine derivatives being about 2.1:1 only.

Worded differently, in this embodiment, the invention pertains to a method for improving and prolonging blood plasma availability and availability to tissue of uridine in a mammal, and/or for treating or preventing (including reducing the risk of) impaired blood plasma and tissue availability of uridine in a mammal, preferably a human being, by orally co-administering soluble sodium and disodium uridine monophosphate (Na2UMP) and/or sodium uridine diphosphate (NaUDP)), optionally in combination with uridine and/or one or more sodium-free uridine derivatives, with the above-mentioned molar ratios (i) and/or (ii) of (added) soluble sodium to uridine. Also, the invention pertains to a (nutritional) composition or kit of parts, preferably a composition, for (therapeutic) use in improving and prolonging blood plasma and tissue availability of uridine in a mammal in need thereof, preferably a human being suffering from impaired blood plasma and tissue uridine levels, and/or for (therapeutic) use in treating or preventing impaired blood plasma and tissue availability of uridine in a mammal, preferably a human being, said kit of parts or composition comprising soluble sodium and disodium uridine monophosphate (Na2UMP) and/or sodium uridine diphosphate (NaUDP)), optionally in combination with uridine and/or one or more sodium-free uridine derivatives, with the above-mentioned molar ratios (i) and/or (ii) of (added) soluble sodium to uridine.

According to these embodiments, the use or method preferably involves the administration of Na2UMP and/or NaUDP, optionally in combination with uridine and/or one or more sodium-free uridine derivatives, wherein the cumulative amount of Na2UMP, NaUDP, uridine and sodium-free uridine derivatives is 30-1000 mg uridine (i.e. theribosyl uracil) per day, preferably about 300-900 mg uridine per day, preferably about 350-800 mg uridine per day, more preferably about 400-750 mg uridine per day. The present method or use preferably comprises the administration of a composition in liquid form, comprising Na2UMP and/or NaUDP, optionally in combination with uridine and/or one or more sodium-free uridine derivatives, wherein the cumulative amount of Na2UMP, NaUDP, uridine and sodium-free uridine derivatives is about 30-1000 mg uridine per ml, preferably about 100-900 mg uridine per 100 ml, preferably about 200-800 mg uridine per 100 ml, more preferably about 300-700 mg uridine per 100 ml. In terms of caloric content, the present method, use and composition preferably comprises the administration of a composition in liquid form, comprising Na2UMP and/or NaUDP, optionally in combination with uridine and/or one or more sodium-free uridine derivatives, wherein the cumulative amount of Na2UMP, NaUDP, uridine and sodium-free uridine derivatives is about 30-1000 mg uridine, preferably about 100-900 mg uridine, more preferably about 200-800 mg uridine, even more preferably about 300-700 mg uridine per 100 kcal based on the total content of the composition administered.

The composition or product or kit preferably further comprises:
  at least one of docosahexaenoic acid (22:6; DHA), eicosapentaenoic acid (20:5; EPA) and docosapentaenoic acid (22:5; DPA), or esters thereof; and/or
  at least one of, or preferably both of:
    choline, or salts or esters thereof; and
    at least one vitamin B selected from the group of vitamin B6, vitamin B12 and vitamin B9, or equivalents thereof, preferably vitamins B6 and B9, most preferably vitamins B6, B9 and B12.

In a preferred embodiment, said composition or product or kit comprises:
  at least one of docosahexaenoic acid (22:6; DHA), eicosapentaenoic acid (20:5; EPA) and docosapentaenoic acid (22:5; DPA), or esters thereof; and/or
  at least one of, preferably both of:
    choline, or salts or esters thereof; and
    at least one vitamin B selected from the group of vitamin B6, vitamin B12 and vitamin B9, or equivalents thereof, preferably vitamins B6 and B9, most preferably vitamins B6, B9 and B12.

In one embodiment, the kit comprises a first part (a) comprising said Na2UMP and/or NaUDP, and a second part (b) comprising said soluble sodium; the further components can be part of either (a) or (b), or provided as additional parts. In a preferred aspect, the composition or product or kit is used in the methods or use of the invention as detailed in the specification. In these embodiments, the term 'added soluble sodium' encompasses all soluble sodium that is provided or present in the composition or product or kit except for the sodium being provided with the UDP and/or UMP. In other words, soluble sodium that is part of Na2UMP or NaUDP is not included in the term 'added soluble sodium'.

In these embodiments, it is preferred that all uridine is provided in the form of Na2UMP and/or NaUDP, preferably Na2UMP.

The method or use according to these embodiments also pertains to improving uridine tissue bioavailability and extending increased tissue levels of uridine, said tissue particularly being brain tissue, using Na2UMP and/or NaUDP, optionally in combination with uridine and/or one or more sodium-free uridine derivatives in molar ratios of soluble sodium to uridine as defined here above.

In these embodiments, it is preferred that the total amount of soluble sodium and uridine, the latter provided as NaUDP and/or Na2UMP, present in the composition or product or kit, or provided in the method or use comply with a molar ratio of total soluble sodium to uridine of at least 3:1, preferably at least 3.5:1, most preferably at least 4:1. While it is preferred to compensate for any loss of sodium when replacing Na2UMP or NaUDP for uridine, even further improvements in terms of blood plasma availability of uridine could be achieved when increasing the co-administration of soluble sodium and uridine in a molar ratio of total soluble sodium:uridine, even beyond the sodium levels already accounted for when using uridine mono- or diphosphates.

Applications

In the above uses or methods, the human being is preferably at increased risk of or suffering from a neurological disorder, preferably a neurodegenerative disorder, preferably a brain disorder, like a dementia, brain ischemia or brain trauma. In particular, the mammal is a human being that suffers from (or is at risk of) a memory and/or cognitive disorder, memory decline and/or cognitive dysfunction, such as Age Associated Memory Impairment (AAMI); Alzheimer's Disease; Parkinson's disease; Pick's disease; and/or dementia, including vascular dementia, frontotemporal dementia, semantic dementia or dementia with Lewy bodies, and Mild Cognitive Impairment (MCI). More particularly, the mammal is a human being that suffers from (or is at risk of) Alzheimer's Disease or dementia. A group of human beings at increased risk of developing neurodegenerative disorders are elderly, preferably of at least 50 years of age, more preferably at least 55 years of age.

In the context of the invention, the human being in need thereof may be a healthy elderly person, preferably of at least 50 years of age, in which case the methods and uses as detailed herein may be non-therapeutic methods and uses, for improving physiological brain uridine levels.

The method, use, kit, combination or compositions as described above preferably further comprise therapeutic amounts of at least one of docosahexaenoic acid (22:6; DHA), eicosapentaenoic acid (20:5; EPA) and docosapentaenoic acid (22:5; DPA), or esters thereof. The method, use, kit or compositions preferably involve at least one of DHA and EPA, preferably at least DHA, most preferably DHA and EPA. DHA is preferably administered in an amount of at least 50 mg per day, more preferably at least 100 mg per day, more preferably 500 to 5000 mg per day, more preferably 750 to 4000 mg per day, most preferably 1000 to 3000 mg per day. If at all, EPA is preferably administered in an amount of at least 30 mg per day, more preferably at least 50 mg per day, even more preferably at least 100 mg per day, more preferably 500 to 5000 mg per day, more preferably 750 to 4000 mg per day, most preferably 1000 to 3000 mg per day. These amounts of EPA apply if it is used alone or, preferably, in combination with DHA. The present composition, combination or kit preferably comprises at least 50 mg per 100 ml, more preferably at least 100 mg per 100 ml, more preferably 500-5000 mg DHA, more preferably 750-4000 mg DHA, even more preferably 1000-3000 mg DHA per 100 ml. In case both DHA and EPA are present, the weight ratio of DHA to EPA is preferably larger than 1, more preferably 2:1 to 10:1, more preferably 3:1 to 8:1. In terms of caloric content, the method, use, kit, combination and composition according to the invention preferably comprise at least 50 mg per 100 kcal, more preferably at least 100 mg per 100 kcal, more preferably 500-5000 mg DHA, more preferably 750-4000 mg DHA, even more preferably 1000-3000 mg DHA per 100 kcal, based on the total caloric content of the composition or combination.

The method, use, kit, combination or composition preferably further comprises therapeutic amounts of choline, or a salt or ester thereof. It is preferred that the choline is present as such, or as choline equivalent in the form of e.g. salt or ester form, or any combination thereof. It is preferably a choline salt. The choline salt is preferably selected from choline chloride, choline bitartrate, or choline stearate. The choline ester is preferably selected from a phosphatidylcholine and lyso-phosphatidyl choline. The present method or use preferably comprises the administration of more than 50 mg choline per day, preferably 80 to 3000 mg choline per day, more preferably 100 to 2000 mg choline per day, most preferably 150 to 1000 mg choline per day. The present composition, combination or kit preferably comprises 80 mg to 3000 mg choline per 100 ml of the composition or combination, preferably 100 mg to 2000 mg choline per 100 ml, preferably 200 to 1000 mg choline per 100 ml, most preferably 200 mg to 600 mg choline per 100 ml. The above numbers are based on choline, the amounts of choline equivalents or sources can be calculated taking the molar equivalent to choline into account.

The method, use, kit, combination or composition preferably further comprises therapeutic amounts of one or more B vitamin(s) from the group selected from vitamins B6, B9 and B12, functional equivalents are encompassed within these terms. Preferably, B vitamins in the context of the invention comprises at least one, more preferably at least two, selected from the group of vitamin B6, vitamin B12 and vitamin B9. More preferably the composition comprises at least vitamin B6 and/or B9, most preferably vitamin B6, B9 and B12.

Vitamin B may be administered in an effective dose, which dose depends on the type of vitamin B used. As a rule of thumb, a suitable minimum or a maximum dose may be chosen based on known dietary recommendations, for instance as recommended by Institute of Medicine (IOM) of the U.S. National Academy of Sciences or by Scientific Committee on Food (a scientific committee of the EU), the information disclosed herein and optionally a limited amount of routine testing. A minimum dose may be based on the estimated average requirement (EAR), although a lower dose may already be effective. A maximum dose usually does not exceed the tolerable upper intake levels (UL), as recommended by IOM.

When present in the composition, combination, kit or method or use according to the invention, vitamin B6 is preferably present in an amount to provide a daily dosage in the range of 0.1 to 100 mg, in particular in the range of 0.5 to 25 mg, more in particular in the range of 0.5 to 5 mg. The present composition or combination preferably comprises 0.1 to 100 mg vitamin B6 per 100 ml, more preferably 0.5 to 5 mg vitamin B6 per 100 ml, more preferably 0.5 to 5 mg vitamin B6 per 100 ml.

When present in the composition, combination, kit or method or use according to the invention, the vitamin B9 is preferably present in an amount to provide a daily dosage in the range of 50 to 5000 µg, in particular in the range of 100 to 1000 µg, more in particular in the range of 200 to 800 µg. The present combination or composition preferably comprises 50 to 5000 µg vitamin B9 per 100 ml, more preferably 100 to 1000 µg vitamin B9 per 100 ml, more preferably 200 to 800 µg folic acid per 100 ml. Vitamin B9 may be present as folate, which includes folic acid, folinic acid, methylated, methenylated and formylated forms of folates, their salts or esters (e.g. C1-6 alkyl ester), as well as their derivatives with one or more glutamic acid, and all in either reduced or oxidized form. Preferably, vitamin B9 is provided as folic acid.

When present in the composition, kit or method or use according to the invention, the vitamin B12 is preferably present in an amount to provide a daily dosage in the range of 0.5 to 10,000 µg, more preferably 0.5-100 µg, in particular in the range of 1 to 10 µg, more in particular in the range of 1.5 to 5 µg. The present combination or composition preferably comprises 0.5 to 100 µg vitamin B12 per 100 ml, more preferably 1 to 10 µg vitamin B12 per 100 ml, more preferably 1.5 to 5 µg vitamin B12 per 100 ml.

The method, use, kit, combination or composition preferably further comprises therapeutic amounts of phospholipids, preferably one or more phospholipid(s) selected from the group consisting of phosphatidic acid (PA), phosphatidylethanolamine (PE), phosphatidylcholine (PC), phosphatidylserine (PS) and phosphoinositides (PI). The composition, combination or kit preferably comprises at least one phospholipid in an amount of 0.01 to 1 gram per 100 ml, more preferably between 0.05 and 0.5 gram per 100 ml, most preferably 80 to 600 mg per 100 ml. The at least one phospholipid is preferably provided by lecithin.

The method, use, kit, combination or composition preferably further comprises therapeutic amounts of antioxidants, preferably selected from vitamin C, vitamin E and selenium, preferably at least vitamin C and vitamin E, most preferably vitamin C, vitamin E and selenium. Antioxidants are preferably included as these may prevent oxidative damage resulting from dietary PUFAs.

Vitamin C includes functional equivalents thereof, and may be present in an amount to provide a daily dosage in the range of 20 to 2000 mg, in particular in the range of 30 to 500 mg, more in particular in the range of 75 to 150 mg. In one embodiment, vitamin C is present in an amount in the range of 20 to 2000 mg, in particular in the range of 30 to 500 mg, more in particular in the range of 75 to 150 mg per 100 ml.

Vitamin E refers to compounds having vitamin E activity as known in the art, typically tocopherol and/or an equivalent thereof. Vitamin E may be present in an amount to provide a daily dosage in the range of 10 to 300 mg, in particular in the range of 30 to 200 mg, more in particular in the range of 35 to 100 mg. Such amounts of vitamin E prevent oxidative damage to the injury site resulting from dietary PUFA present in the composition according to the invention. In one embodiment, tocopherol and/or equivalent is present in an amount in the range of 10 to 300 mg, in particular in the range of 30 to 200 mg, more in particular in the range of 35 to 100 mg per 100 ml of the composition. The term "tocopherol and/or an equivalent thereof", as used in this description, comprises tocopherols (e.g. alpha- and gamma-), tocotrienols, pharmaceutical and/or nutritional acceptable derivatives thereof and any combination thereof. The above numbers are based on alpha-tocopherol equivalents (alpha-TE), as recognized in the art.

The antioxidant activity of selenium advantageously prevents and/or inhibits damages to the brain areas. Selenium is preferably applied in amounts of between 0.01 and 5 mg selenium per 100 ml, preferably between 0.02 and 0.1 mg selenium per 100 ml. The amount of selenium administered per day is preferably more than 0.01 mg, more preferably 0.01 to 0.5 mg.

The invention preferably pertains to a method, use, composition or combination as defined here above, comprising therapeutic amounts of DHA, choline, vitamins B6, B9 and B12, vitamin C, vitamin E and selenium, with the aforementioned uridine and molar ratio of soluble sodium and uridine.

The composition or combination according to the invention may be part of a nutritional product, for example a nutritional supplement, e.g., an additive to a normal diet, a fortifier (to be added to a normal diet) or a complete nutrition.

The compositions or combinations as described above can be used as part of nutritional therapy, nutritional support, as a medical food, as a food for special medical purposes or as a nutritional supplement. The composition or combination can be consumed in one, two or three servings between 75 and 200 ml per day or per unit, most preferably between 90 and 150 ml/day, most preferably about 125 mL per day in the aforementioned applications.

The invention preferably pertains to a method, use, composition or combination as defined here above, comprising administering, per daily dosage or per 125 ml, in addition to the uridine and molar ratio of soluble sodium to uridine as defined here above:

0.1-0.5 g, preferably 0.2-0.4 g EPA,
0.5-2 g, preferably 0.7-1.5 g DHA,
0.1-0.7 g, preferably 0.2-0.6 g choline,
0.05-0.5 g, preferably 0.06-0.2 g phospholipids, and
0.1-0.7 mg, preferably 0.2-0.6 mg folic acid, In one embodiment, the method, use, composition or combination as defined here above further comprises, per daily dosage or per 125 ml:

0.01-0.07 g, preferably 0.02-0.06 g vitamin E (alpha-TE),
0.04-0.12 g, preferably 0.06-0.1 g vitamin C,
0.03-0.09 mg, preferably 0.04-0.08 mg selenium,
1-6 µg, preferably 2-5 µg vitamin B12, and
0.2-5 mg, preferably 0.5-4 mg vitamin B6.

The subjects that can benefit from the method and composition of the invention often experience problems with eating. Their sensory capabilities and/or control of muscles can become imparted, as well as in some instances their ambition to apply proper eating habits. Swallowing and/or mastication may be problematic. Hence, the present composition is preferably provided in the form of an aqueous composition, in particular a drink capable of being ingested through a straw.

Related therewith, the composition, combination or product according to the invention is a ready-to-use product preferably having a low viscosity, preferably a viscosity between 1 and 2000 mPa·s measured at a shear rate of 100 sec−1 at 20° C., more preferably a viscosity between 1 and 100 mPa·s measured at a shear rate of 100 sec−1 at 20° C. In a preferred embodiment the present composition, combination or product has a viscosity of 1-80 mPa·s at a shear rate of 100 per sec at 20° C., more preferably of 1-40 mPa·s at a shear rate of 100 per sec at 20° C. These viscosity measurements may for instance be performed using plate and cone geometry.

To be optimally accepted by the subject, the present combination or composition preferably has an osmolality of 300 to 800 mOsm/kg. However, the energy density of the product is preferably not so high that it interferes with normal eating habits. When in liquid form, it preferably contains between 0.2 and 3 kcal/ml, more preferably between 0.5 and 2, between 0.7 and 1.5 kcal/ml.

EXAMPLES

Example 1

Experimental Study

Animals: New Zealand White rabbits (male) were used, as uridine metabolism of rabbits is even more translatable to humans than the uridine metabolism of rats and mice. Rabbits were held individually housed in suitable rabbit cages on a standard 12/12 hours day/night light regime. The rabbits received standard rabbit chow pellets and water was available ad libitum and hay was provided once a day. All experiments were in accordance to Dutch law on animal testing and approved by local ethic committee.

The rabbits were orally dosed with uridine at 88 mg/kg metabolic weight or uridine 88 mg/kg metabolic weight with either 2× or 4× equimolar concentration of sodium chloride, and before gavage these combinations of uridine and sodium chloride was dissolved in 5 ml ddH$_2$O. Each of the three conditions was tested in each animal, with a wash out period between the experiments of at least one week. On the day of the experiment rabbits were fasted 2 hours before oral gavage. Blood samples were taken by puncture of either the artery or vein of the ear. First blood sample was taken before gavage was placed, this sample was taken as t=0. After oral gavage blood samples were taken at t=30, 60, 90, 120, 150, 180, 240 and 360, 0.5 mL per sample. Until further analysis samples were stored at −80 degrees C.

Determination of uridine: For detection of uridine in blood samples perchloric acid was added. Subsequently uridine was extracted by vortexing the solution. Reversed-phase HPLC was used to separate uridine from other nucleotides/nucleosides, and uridine levels were quantified using the absorbance of the compound at 260 nm, compared to a standard.

For each condition a dose-concentration pharmacokinetic graph was constructed. From this graph the iAUC was calculated using the trapezoidal method. As each condition was tested in each rabbit a paired ANOVA was used as statistical analysis. Dunnett's multiple comparisons was used as posthoc test, with $p<0.05$ as significance level.

Figure 3:
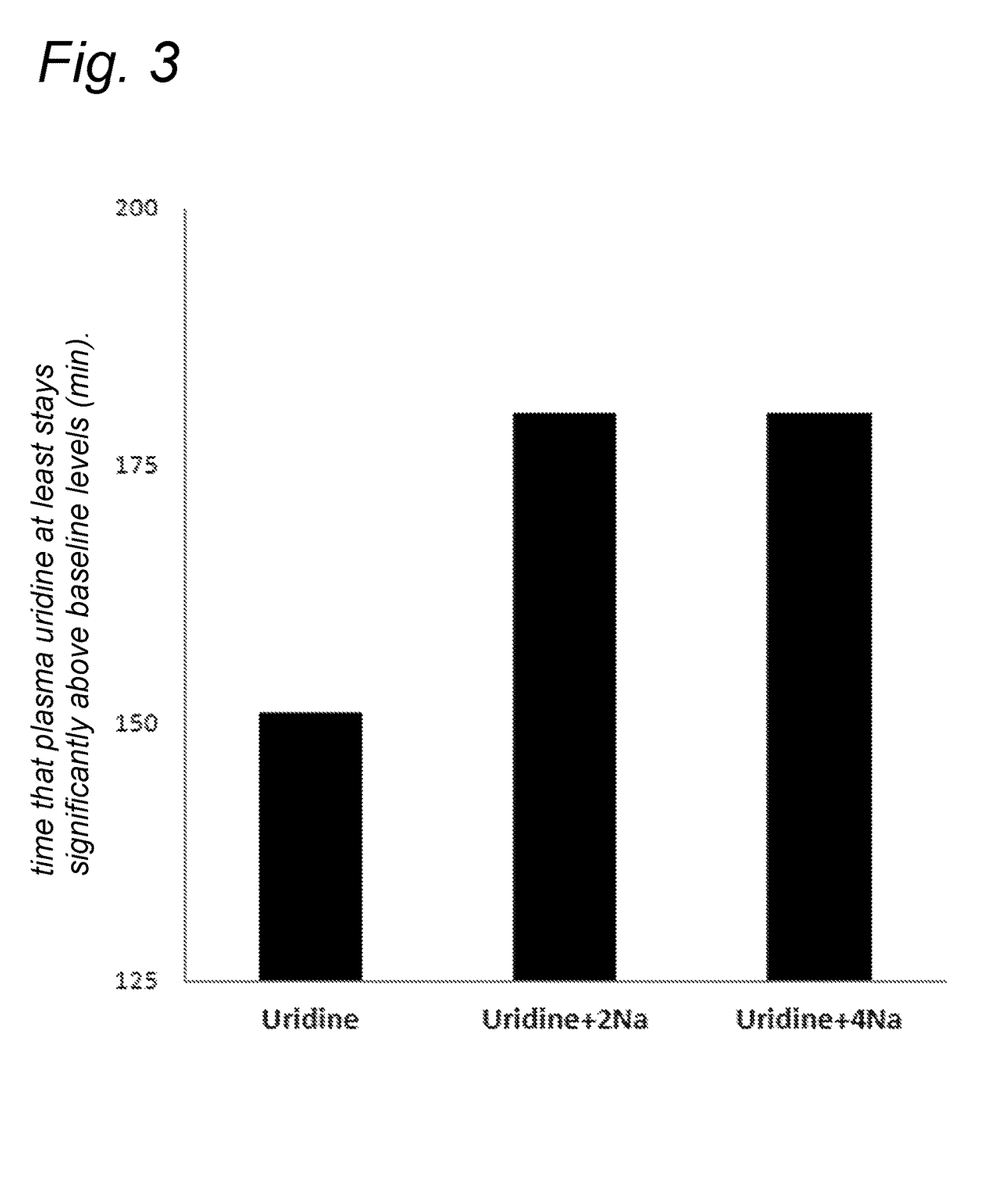
FIG. 3 is a histogram depicting the time point after oral administration of either uridine (Uridine), uridine with two sodium ions per molecule uridine (Uridine+2Na), or uridine with four sodium ions per molecule uridine, (Uridine+4Na) until which blood plasma uridine concentrations stayed statistically significantly above baseline levels. In other words: it shows the time for blood plasma uridine concentrations to return to baseline levels after the oral administration of Uridine, Uridine+2Na or Uridine+4Na. This indicates the blood plasma uridine levels was prolonged using 2 or 4 sodium ions per molecule uridine, compared to Uridine.

Results: The results are plotted in FIGS. 1, 2 and 3: FIG. 1 shows that blood plasma uridine concentrations were increased using increased levels of sodium, and in FIG. 2 it is evidenced that blood plasma uridine levels remained statistically significantly higher than the baseline for longer time(i.e. prolonged blood plasma uridine levels) when sodium levels were increased. At 180 minutes, blood plasma uridine levels from the administration of U alone were no longer statistically significantly above baseline ($p>0.05$), while those of U+2Na ($p=0.05$) and U+4Na ($p<0.05$) were. As FIGS. 1 and 2, FIG. 3 shows that increased levels of sodium help maintaining blood plasma uridine concentrations at elevated levels for a longer time, the time over which these concentrations return to baseline (no longer significantly different) is higher for U+2Na (180 min) than for U alone (151 min), and—with an eye on FIGS. 1 and 2—even longer for U+4Na. At 180 minutes the blood plasma uridine concentration is more statistically significantly above baseline for U+4Na ($p<0.05$) than U+2Na ($p=0.05$) (FIG. 2).

The invention claimed is:

1. A method for:
   (i) therapeutically improving and prolonging blood plasma uridine levels and tissue availability of uridine; and/or
   (ii) treating disorders associated with impaired blood plasma and tissue availability of uridine,
   in a human being in need thereof, wherein the method comprises orally administering to the human being a composition comprising:
   (a) sodium in a form soluble in water; and
   (b) 1-[2R,3R,4S,5R)-3,4-dihydroxy-5-(hydroxymethyl)oxolan-2-yl]pyrimidine-2,4-dione (uridine),
   in a molar ratio of sodium in a form soluble in water: uridine of more than 1.5:1, and up to 3:1.

2. The method according to claim 1, wherein the human being is suffering from neurological disorders, diabetes, insulin resistance, stroke, endothelial damage, or fatty liver.

3. The method according to claim 2, wherein the neurological disorders comprise neurodegenerative disorders or brain trauma.

4. The method according to claim 1, wherein the human being suffers from a memory and/or cognitive disorder, memory decline and/or cognitive dysfunction, Alzheimer's disease, Parkinson's disease, Pick's disease, dementia, and/or Mild Cognitive Impairment (MCI).

5. The method according to claim 4, wherein the human being suffers from Alzheimer's Disease or dementia.

6. The method according to claim 1, wherein the uridine is administered in an amount of 30-1000 mg per day.

7. The method according to claim 1, comprising further administering at least one of docosahexaenoic acid (22:6; DHA), eicosapentaenoic acid (20:5; EPA) and docosapentaenoic acid (22:5; DPA), or esters thereof.

8. The method according to claim 7, comprising administering at least DHA, in an amount of 500 to 5000 mg per day.

9. The method according to claim 1, wherein the tissue is brain tissue.

10. The method according to claim 1, wherein the composition further comprises:
    (c) choline, or salts or esters thereof; and
    (d) at least one vitamin B selected from the group of vitamin B6, vitamin B12 and vitamin B9.

11. The method according to claim 10, the composition comprising at least vitamins B6 and B9.

12. The method according to claim 1, wherein the molar ratio of sodium in a form soluble in water:uridine is in the range of 2:1 to 3:1.

* * * * *